| United States Patent [19]
Morishige | [11] Patent Number: 4,851,390
[45] Date of Patent: Jul. 25, 1989 |

[54] NUTRITIONAL METHODS UTILIZING COMPOSITIONS CONTAINING RNA, CA+2, MG+2 AND/OR ASCORBATE

[75] Inventor: Fukumi Morishige, Tokyo, Japan

[73] Assignee: Nissan Chemical Industries, Ltd., Tokyo, Japan

[21] Appl. No.: 896,804

[22] Filed: Aug. 15, 1986

[30] Foreign Application Priority Data

Aug. 16, 1985 [JP] Japan ................... 60-180146

[51] Int. Cl.$^4$ ............... A61K 31/375; A61K 33/06; A61K 31/665
[52] U.S. Cl. ....................... 514/44; 514/47; 514/48; 514/51; 536/27; 536/28; 536/29; 424/682; 424/695; 549/315
[58] Field of Search ............. 514/44, 47, 48, 51

[56] References Cited

U.S. PATENT DOCUMENTS 3,341,412  9/1967  O'Hallaron et al. ............ 514/48
3,484,521 12/1969  Glasky ........................... 514/47

FOREIGN PATENT DOCUMENTS 2068415  8/1971  France ........................ 514/44
0029230  8/1973  Japan ......................... 514/48
0073524  9/1984  Japan ......................... 514/48
0136515  7/1985  Japan ......................... 514/44

OTHER PUBLICATIONS

Benzi et al., Biochemical Pharmacology, vol. 32(6), pp. 1083–1091 (1983).
Benzi et al., Biochemical Pharmacology, vol. 28, pp. 2845–2850 (1979).

*Primary Examiner*—Ronald W. Griffin
*Assistant Examiner*—L. Eric Crane
*Attorney, Agent, or Firm*—Oliff & Berridge

[57] ABSTRACT

Disclosed is a nutritional agent for cerebrospinal nerves comprising ribonucleic acid, ribonucleotide and/or ribonucleoside. It is effective for the alleviation and recovery of conditions of cerebrospinal degenerative diseases such as epilepsy, Parkinson's disease and an attack of convulsion.

20 Claims, No Drawings

NUTRITIONAL METHODS UTILIZING COMPOSITIONS CONTAINING RNA, CA+2, MG+2 AND/OR ASCORBATE

BACKGROUND OF THE INVENTION

1. Field of the Invention

This invention relates to a nutritional agent which promotes recovery from conditions of cerebrospinal degenerative diseases, such as epilepsy, an attach of convulsion, brain degenerative disease, cranial nerve disease, cerebral basal ganglion disease, cerebellar degenerative disease, spinal degenerative disease and muscular disease.

2. Description of the Prior art

In recent years, there has been a striking advance in the diagnostic and therapeutic techniques in the field of cranial nerve surgery for example CT (computer tomography) scanning, ultrasonication, cerebral angiography and microsurgery, but there have been few satisfactory therapeutic agents for dementia hypomnesia, epilepsy, an attack of convulsion, etc. which are due to a decrease in the function of nervous cells of the brain.

SUMMARY OF THE INVENTION

In view of the above state of the art, the present invention provides a nutritional agent useful for the promotion of recovery of cerebrospinal diseases, which comprises ribonucleic acid (to be referred to as RNA), ribonucleotide and/or ribonucleoside derived from yeast.

Examples of the cerebrospinal degenerative diseases are epilepsy, an attack of convulsion, brain degenerative disease, cranial nerve disease, cerebral basal ganglion disease, cerebellar degenerative disease, and muscular diseases. The present inventors searched and studied a nutritional agent which improves these conditions. Unexpectedly, the present inventors have found that by orally administering a nutritional agent comprising RNA, ribonucleotide and/or ribonucleoside to the patient of such a condition, the condition is improved and the present invention is accomplished.

Specific examples of cerebrospinal degenerative disease on which the nutritional agent of this invention is effective include; epilepsy, an attack of convulsion, and brain degenerative diseases, for example degenerative diffuse sclerosis, such as; Pelizaeus-Merzbacher disease, Sholtz disease, Krabbe disease, and other congenital hereditary diseases such as; amaurotic familiar, Rourence-Moon-Bordet-Bied syndrome, Hurler syndrome, cerebral disease in the old age and in the early old age (such as senile demenntia, Alzheimer disease, and Pick disease), and cranial nerve disease, such as; progressive bulbar palsy, progressive paralysis of ocular muscles, hereditary nystagmus, Adie syndrome, syringobulbia, Leber disease and cerebral basal ganglion disease, such as; Parkinson's disease, Chorea, dystonia syndrome, ethetosis syndrome, myoclonia syndrome, artuun parkinsonism, degenerative diseases of the cerebellum such as; hereditary, spinal and cerebellar ataxis, hereditary ataxia with myoatrophy, muscular diseases, such as; progressive muscular dystrophy, myoastenia, and periodic paralysis.

RNA, ribonucleotide and/or ribonucleoside in the nutritional agent of this invention mean RNA, ribonucleotide, or ribonucleoside; RNA and ribonucleotide; RNA and ribonucleoside; ribonucleotide and ribonucleoside; and RNA, ribonucleotide and ribonucleoside.

RNA, ribonucleotide and/or ribonucleoside as active ingredients of the nutritional agent of this invention (to be referred to as RNA, etc.) may be of natural origin or synthetic materials.

RNA, etc. of natural origin mean those obtained from microbial cells, preferably RNA, etc. extracted and fractionated from yeasts such as brewer's yeast, baker's yeast, Torula yeast and lactic yeast, especially preferably RNA, etc. extracted from brewer's yeast.

The method of obtaining RNA, etc. of natural origin is exemplified by the following method starting from brewer's yeasat.

The residue resulting from removal of water-soluble low-molecular-weight fractions from a slurry-like (solids content abou 10% by weight) or dry yeast recovered from the beer producing process is used as a starting material. An aqueous soslution of sodium chloride is added to the residue, and RNA is extracted under heat. Concentrated hydrochloric acid is added to the extract to form a parecipitate. After neutralization, extraction is again effected by adding water. Then, an organic solventt such as ethanol, is added to precipitate RNA. The supenatant is removed by centrifugal separation and a precipitated fraction composed mainly of RNA is obtained. It is then dried by a suitable conventional method.

The approximate composition of brewer's yeast RNA after drying is as follows:

TABLE

| Ingredient | Content (dry base) |
| --- | --- |
| RNA(*1) | 65–95% by weight |
| CAS(*2) | less than 5 |
| DNA | less than 1 |
| Proteins | less than 22 |
| Sugar (hexose) | less than 18 |
| Sodium chloride | less than 0.5 |

(*1):Molecular weight about $1.3 \times 10^4$
(*2):Low-molecular weight ribonucleic acid, ribonucleotide and ribonucleoside which are soluble in 5% cold perchloric acid.

The oral toxicity to mice of ribonucleic acid extracted from yeast canb e said to be very low since it exerts no action even when administered in a dose of 5250 mg/kg.

The nutritional agent in accordance with this invention comprises RNA, etc., or a mixture of RNA, etc. with at least one suitable nutritionally or pharmacologically acceptable adjuvant such as a binder (syrup, gum arabic, gelatin, sorbitol, tragacanth, polyvinlypyrrolidone, etc.), a vehicle (lactose, sugar, corn starch, calcium phosphate, sorbitol, glycine, etc.), a lubricant (magnesium stearate, talc, polyethylene glycol, silica, etc.), a disintegrant (potato starch, etc.), and a flavor or a sweetener (sugar, aspartame, saccharin, etc.) in the form of a powder, granule, tablets or capsules.

The nutritional agent of this invention is desirably administered orally.

The dosage for administration to adults is 0.1g to 10.0 g. preferably 0.5 to 5.0 g as RNA, etc. once, or two or three times in divided dosages, daily. The dosage, however, may be increased or decreased depending upon the age, body weight, condition, etc., of the patient.

Addition of pharmaceutically acceptable calcium and magnesium salts to RNA, etc. tends to enhance the nutritional or pharmacological activity of RNA, etc. Examples of these pharmaceutically acceptable calcium and magnesium salts are those in which the acid portion is almost inert pharmacologically and the metal ion portion alone can be expected to have activity, such as calcium lactate and magnesium sulfate. The weight ratio of these salts to the total weight RNA, etc. depends upon the weight of the calcium or magnesium portion, and is, for example, 1 to 5 for calcium lactate, and 1 to 5 for magnesium sulfate.

When nutritional agent of this invention is administered in admixture with ascorbic acid, sodium ascorbate, or calcium ascorbate, the uric acid value of the blood tends to decrease from that in the absence of such an additional compound. THus, with patients of such a constitution that the administration of the nutritional agent of this invention tends to ncnrease the uric acid value, symptom of gout which may be induced by the rise of hte blood uric acid value can be avoided.

The ratio of ascorbic acid, sodium ascorbate or calcium ascorbate to the total weight of RNA, etc. is from 0.5 to 10, preferably from 1 to 5.

DETAILED DESCRIPTION OF THE INVENTION

The present invention will be described in greater detail on the basis of the following examples. It should be understood however that the invention is not limited to these examples. All percentages in these examples are by weight.

PRODUCTION EXAMPLE 1

(1) The slurry-like yeast recovered from the beer production process as passed through a sieve having a size of 80 to 200 mesh to remove solids. The residue was washed with an aqueous solution of sodium carbonate and then water to obtain a raw yeast free of bitter taste.

(2) Sodium chloride and water were added so as to provide a yeast concentration of 10% and a sodium chloride concentration of 10%. The mixture was heated and boiled for 2 to 5 hours. Instead of this boiling, autoclaving for 1 hour may be carried out.

(3) Ribonucleic acid was extracted under boiling. Cooling and solid-liquid separation by a centrifugal separator or the like gaven an extract.

The solid containing ribonucleic acid was washed with 10% sodium chloride solution, and the wash liquor was recovered and combined with the extract.

(4) Concentrated hydrochloric acid was added to this extract to adjust to pH 2, and a fraction precipitated under acidity was obtained. The fraction was separated and recovered, and sodium hydroxide was added to form a precipitate again. Since this precipitate was rapidly formed, the supernatant was removed, and the recipitate was recovered by a centrifugal separator. The resulting extract was dehydrated with 98% ethanol and washed, and dried by a suitable method.

PRODUCTION EXAMPLE 2

Water (450 liters) was added to 90 kg of dry brewer's yeast, and the mixture was stirred for a predetermined period of time to solubilize impurities and wash the yeast.

The mixture was then centrifuged to recover washed yeast. Water (800 liters) and 90 kg of sodium chloride were added, and the mixture was heated. The mixture was boiled for 2 hours and subjected to a centrifugal separator. The residue containing ribonucleic acid was washed with 10% aqueous sodium chloride solution, and the wash liquor was recovered. The wash liquor was combined with the extract. By performing the same treatment as (4) of Production Example 1, RNA extract was obtained.

PRODUCTION EXAMPLE 3

A slurry-like brewer's yeast was freed of a bitter taste, washed by a cutomary method and dried on a drum dryer at 120° C. to 140° C. Hot water at a temperature of 95° C. or higher was added to the dry brewer's yeast in an amount by weight ten times the latter. The mixture was maintained for 5 minutes, and subjected to solid-liquid separation to obtain a solid. Sodium chloride and water were added to the solid, and the concentration of the solid brewer's yeast and the concentration of sodium chloride were each adjusted to 10%. The solution was fed to a homogenizer so that the discharge pressure became at least 600 kg/cm$^2$ in order to crush the cellular wall. The treated liquid containing the crushed yeast was heated and boiled for 2 to 5 hours, and thereafter, the same treatments as in (3), and (4) of Production Example 1 were performed to obtain crude ribonucleic acid.

The results of analyzing the compositions of crude RNAs obtained by these Production Examples are shown in the following table.

| Production Example | 1 | 2 | 3 |
| --- | --- | --- | --- |
| Yield (%) of crude ribonucleic acid | 1.51 | 2.57 | 3.09 |
| Components (%) of crude ribonucleic acid | | | |
| CAS fraction* | 3.0 | 6.0 | 5.4 |
| ribonucleic acid fraction* | 87.4 | 77.1 | 85.6 |
| DNA fraction* | 0 | 1.2 | 1.32 |

*These components were fractions analyzed by the Schmidt Townhouser and Schnider method (STS method) (Food Analysis Method edited by the Committee of Editing Food Analysis Methods, Japanese Society of Food Industry, p. 563, 1982). CAS is an acid-soluble low-molecular-weight ribonucleic acid of nucleotide and nucleoside.

TEST EXAMPLE 1

Acute Toxicity Test:

Brewer's yeast RNA (RNA content 70%) obtained in accordance with the method of Production Example 1 was tested for acute toxicity by forced oral administration to mice (ICR strain, 40 males and 40 females). Before administration, the animals were caused to fast for 18 hours. A suspension of 7500 mg (5250 mg calculated as RNA) of the brewer's yeast in 50 ml of water was administered per kilogram of the animals, and then the animals were observed for 14 days. But no abnormality was noted.

In the following Clinical Examples, RNA represents the total amount of RNA(*1) and CAS(*2) described in the table on page 4. The brewer's yeast RNA was produced from the material produced in accordance with Production Example 1.

CLINICAL EXAMPLE 1

Example of promotion of recovery of a patient with epilepsy:

The patient was a 7-year old girl with the following history. About 1 year ago, she got epilepsy. Nearly extreme doses of an antiepileptic were administered, but epileptic convulsion was not cured and the condition was not improved. The doctor told the parents that prognosis was bad. She was unable to take foods, and nutrition was maintained through a stomach tube. Her consciousness was not clear but always hypalgesic. She incessantly repeated epileptic convulsion. Brain computer tomography showed marked enlargement of the ventricle and compression and atrophy of the brain.

An agent containing the brewer's yeast RNA (RNA content 70%) was administered to the patientn in a dose of 3 g/day in three divided dosages over the cource of 6 months. One week after the starting of administration of the brewer's yeast RNA, epileptic convulsion was not observed. A basal drainage was inserted in order to remedy the enlargement of the ventricle. After about 40 days, the patient was allowed to leave the hospital. Thereafter, an agent containing brewer's yeast RNA (RNA content 70%) was administered in the same dosage as above. The patient became able to take foods by her own power, and began to laugh. About 6 months after the starting of administration of the RNA-containing agent, epileptic convulsion disappeared entirely.

CLINICAL EXAMPLE 2

Example of treating Parkinson's disease:

The patient was an 81-year old person with Parkinson's disease and had the following history. A reduction in spontaneity, urine incontinence, a light degree of dementia and derangements in emotion and volition were noted, and the patient used a wheeled chair. The patient was treated with drugs, including E-C-dopal (levodopa), ARTANE (trihexyphenidyl hydrochloride) and Uvela- N (Nicatinic acid +vitamin E) and with exercise rehabilitation, but no significant effect was noted.

An agent containing brewer's yeast RNA (RNA content 70%) was administered to the patient in a dose of 3 g per day in three divided dosages over the course of 3 months. The patient regained his ability to walk by himself, and increased feeling, action and spontaneity were also observed. For example, the patient could go to a nearby dentist or go shopping in nearby stores.

(Nuclear $C_{RS}$ in the following clinical example was produced from the material produced in accordance with Production Example 1. The definition of RNA was the same as in the above Clinical Examples.)

CLINICAL EXAMPLE 3

Example of reduction in the attach of convulsions:

The patient was a two-year old infant who was born by uneventful delivery. The patient was infected with encephalitis by viral infection (herpes I type) seven months after birth. Two to three months after infection, an attach of convulsion occurred in the patient. An anticonvulsant was administered but found to be ineffective. Hemiplegia occurred as a complication, and an epileptic attack lasted for a whole day. Nutrition was administered through a stomach tube.

The results of diagnosis about 2 years after birth were as follows:

"Incessant convulsion was observed, and the patient was senseless. Hemiplegia was noted, and the Babinski reflex was weakly positive. Brain computer tomography showed that the right temporal lobe was close to the Sylvian's fissure, and a low concentration was observed, and that no enlargement of the ventriculus lateralis cerebri was noted".

About three spoonfuls (about 5.4 g; containing 1.4 g of RNA derived from brewer's yeast and 3.0 g of vitaminn C) of Nuclear $C_{RS}$, 1.0 g of calcium lactate and 1.0 g of magnesium sulfate were administered to the patient per day, but convulsion did not decrease.

Beginning approximately on the 50th day after starting the administration of the RNA-containing agent, about 6 spoonfuls (about 10.8 g containing 2.7 g of RNA derived from brewer's yeast and 6.0 g of vitamin C) of Nuclear $C_{RS}$, 2.0 g of calcium lactate, and 2.0 g of magnesium sulfate per day were administered. By diagnosis two weeks later, the convulsion was markedly reduced. Thirty convulsions per day now decreased to between 10 and 14 convulsions per day, his facial expression improved, and he became of good temper. About 4 months and 20 days after starting the administration of the RNA-containing agent, the attack of convulsion showed a further tendency to decrease.

CLINICAL EXAMPLE 4

Example of decreasing attacks of convulsion:

The patient was a 21-year old male infected with viral meningitis during infancy:

The patient was first treated with a general anti-convulsant, but an attack of convulsion continued. He was raised in a certain institution.

The patient was hospitalized, and six spoonfuls (about 10.8 g containing 2.7 g of RNA derived from brewer's yeast and 6.0 g of vitamin C) of Nuclear $C_{RS}$, 180 mg vitamin $B_6$(V$B_6$), 3 g vitamin $B_3$ (V$B_3$) (bulk), 2.0 g of calcium lactate and 2.0 g of magnesium sulfate were administered daily.

About one month after starting the administeration of the RNA-containing agent, the attacks were alleviated. Since the anticonvulsant was of the barbiturate type, the patient tended to be drowsy. Gradually, the administration of the drugs previously taken was stopped, and 6 spoonfuls (about 10.8 g containing 2.7 g of RNA derived from brewer's yeast and 6.0 g of vitamin C) of Nuclear $C_{RS}$, 180 mg of V$B_6$, 3 g of V$B_3$ (bulk), 2.0 g of calcium lactate and 2.0 g of magnesium sulfate (not containing any anticonvulsant) were administered daily. About two months after starting the administration of the RNA-containing agent a tendency toward particularly frequent convulsion during fever has disappeared.

CLINICAL EXAMPLE 5

Example of decreasing attacks of convulsion:

At the time of delivery, the umbilical cord wrapped around the neck portion of the patient and was born in a syncoptic state, but resuscitation was successful.

About 2 months after birth, convusion occurred and continued to date. An anticonvulsant was administered by a nearby physician, but was not effective. As a result of high doses of a strong sedative, particularly a barbiturate preparation, the patient always shows a dorwsy tendency. Nutrition is administered through the stomach tube.

The results of diagnosis about 8 months and 25 days after birth were as follows:

Muscular hypertonicity of the entire body was noted. Primitive reactions which should disappear at this age, such as Moro reflex, grasp reflex, and plantar reflex remained to some extent, but no sucking reflex. The Babinski reflex which as this age shows a disturbance of the pyramidal tract was observed only at the left lower extremity. The patient could not sit down alone, or toss on a bed. His eyesight was disturbed.

About onen spoonful (about 1.8 g containing 0.5 g of RNA derived from brewer's yeast and 1.0 g of vitamin C) of Nuclear $C_{RS}$ was administered orally to this patient three times daily, and at the same time, 1.0 go of calcium lactate and 1.0 g of magnesium sulfate were administered. Anticonvulsants prescribed by a physician were administered but not a barbiturate preparation. The attack of convulsion gradually decreased markedly, and therefore, the anticonvulsants were further decreased. But convulsion did not increase, while the patient previously was always drowsy, he began to laugh upon been called and stand up about 2 months after the administration of the RNA-containing agent was begun. Furthermore, the patient began to play with toys, and asked for maternal affection.

About two months after starting the administration of the RNA-containing agent, convulsions were reduced to one per day while the patient was awake.

Formulation examples are shown below. The definition of RNA was the same as in the above Clinical Examples.

FORMULATION EXAMPLE 1

One gram of brewer's yeast RNA obtained by the method of Production Example 1 was enveloped in one pack.

FORMULATION EXAMPLE 2

Sodium ascorbate (3.0 g) was mixed with 1.0 g of brewer's yeast RNA obtained by the method of Production Example 1, and the mixture was enveloped in one pack.

FORMULATION EXAMPLE 3

Brewer's yeast RNA (1.0 g obtained by the method of Production Example 1 was mixed with 3.0 g of sodium ascorbate, 1.0 g of calcium lactate and 1.0 g of magnesium sulfate, and the mixture was enveloped into one pack.

FORMULATION EXAMPLE 4

Brewer's yeast RNA (1.0 g) obtained by the method of Production Example 1 was mixed with 1.0 g of calcium lactate and 1.0 g of magnesium sulfate, and the mixture was enveloped into one pack.

As is clearly seen fromthe foregoing Clinical Examples, the nutritional agent of this invention is effective for promoting improvement and recovery of conditions of cerebrospinal degenerative diseases, such as epilepsy, Parkinson's disease and an attack of convulsion.

We claim:

1. A method of alleviating or stopping an attack of epilepsy in a human comprising: administering to a human suffering from epilepsy a nutritional agent containing ribonucleic acid, said acid having a purity of at least 65% and in an amount effective to alleviate or stop an epileptic attack.

2. The method of claim 1, wherein the attack of epilepsy is an attack of symptomatic epilepsy.

3. The method of claim 1, wherein the attack of epilepsy is an attack of genuine epilepsy.

4. The method of claim 1 wherein said ribonucleic acid is extracted from yeast.

5. The method of claim 4 wherein said yeast is brewer's yeast.

6. The method of claim 1 wherein said nutritional agent further comprises a pharmaceutically acceptable salt of calcium and magnesium.

7. The method of claim 1 wherein said nutritional agent further comprises a member selected from the group consisting of ascorbic acid, sodium ascorbate or calcium ascorbate.

8. A method of alleviating or stopping the symptoms of Parkinson's disease in a human comprising: administering to a human suffering from Parkinson's disease a nutritional agent containing ribonucleic acid, said acid having a purity of at least 65% and in an amount effective to alleviate or stop the symptoms of Parkinson's disease.

9. The method of claim 8 wherein said ribonucleic acid is extracted from yeast.

10. The method of claim 9 wherein said yeast is brewer's yeast.

11. The method of claim 8 wherein said nutritional agent further comprises a pharmaceutically acceptable salt of calcium or magnesium.

12. The method of claim 8 wherein said nutritional agent further comprises a member selected from the group consisting of ascorbic acid, sodium ascorbate or calcium ascorbate.

13. A method of alleviating or stopping an attack of convulsions in a human comprising: administering to a human suffering from attacks of convulsions a nutritional agent containing ribonucleic acid, said acid having a purity of at least 65% and in an amount effective to alleviate or stop the convulsions.

14. The method of claim 13 wherein sid ribonucleic acid is extracted from yeast.

15. The method of claim 14 wherein said yeast is brewer's yeast.

16. The method of claim 13 wherein said nutritional agent further comprises a pharmaceutically acceptable salt of calcium or magnesium.

17. The method of claim 13 wherein said nutritional agent further comprises a member selected from the group consisting of ascorbic acid, sodium ascorbate or calcium ascorbate.

18. A method of alleviating senile dementia inn a human, comprising: administering to a human suffering from senile dementia a nutritional agent containing ribonucleic acid extracted from brewer's yeast, said acid having a purity of at least 65% and in an amount effective to alleviate senile dementia.

19. The method of claim 18 wherein said nutritional agent further comprises a pharmaceutically acceptable salt of calcium or magnesium.

20. The method of claim 18 wherein said nutritional agent further comprises a member selected from the group consisting of ascorbic acid, sodium ascorbate or calcium ascorbate.

* * * * *